March 2, 1943. J. J. GRULLEMANS Plant Pat. 568

HYPERICUM

Filed Sept. 5, 1942 2 Sheets-Sheet 1

WITNESS
Addison E. Avery

John J. Grullemans,
INVENTOR,
by: John Harrow Kronquist,
his attorney.

March 2, 1943. J. J. GRULLEMANS Plant Pat. 568

HYPERICUM

Filed Sept. 5, 1942 2 Sheets-Sheet 2

WITNESS

Addison E. Avery

INVENTOR,

John J. Grullemans, by

John Harrow Leonard, his attorney.

Patented Mar. 2, 1943

Plant Pat. 568

UNITED STATES PATENT OFFICE

568

HYPERICUM

John J. Grullemans, Painesville, Ohio, assignor to The Wayside Gardens Company, Mentor, Ohio, a corporation of Ohio Application September 5, 1942, Serial No. 457,440

1 Claim. (Cl. 47—60)

This invention relates to a new variety of Hypericum.

The variety was produced through the reciprocal crossing of the *Hypericum patulum* Henri and the *Hypericum elatum*. The plant was first produced in the spring of 1935 in the fields of The Wayside Gardens Company at Mentor, Lake County, Ohio, and, beginning in the spring of 1936 and continuously since, it has been reproduced asexually true to form by soft wood cuttings.

A specimen of the new variety is illustrated in the drawings in which—

Fig. 3 is a sketch of a typical blossom;

Fig. 4 is a color illustration of a ripe seed carpel.

Figure 1:
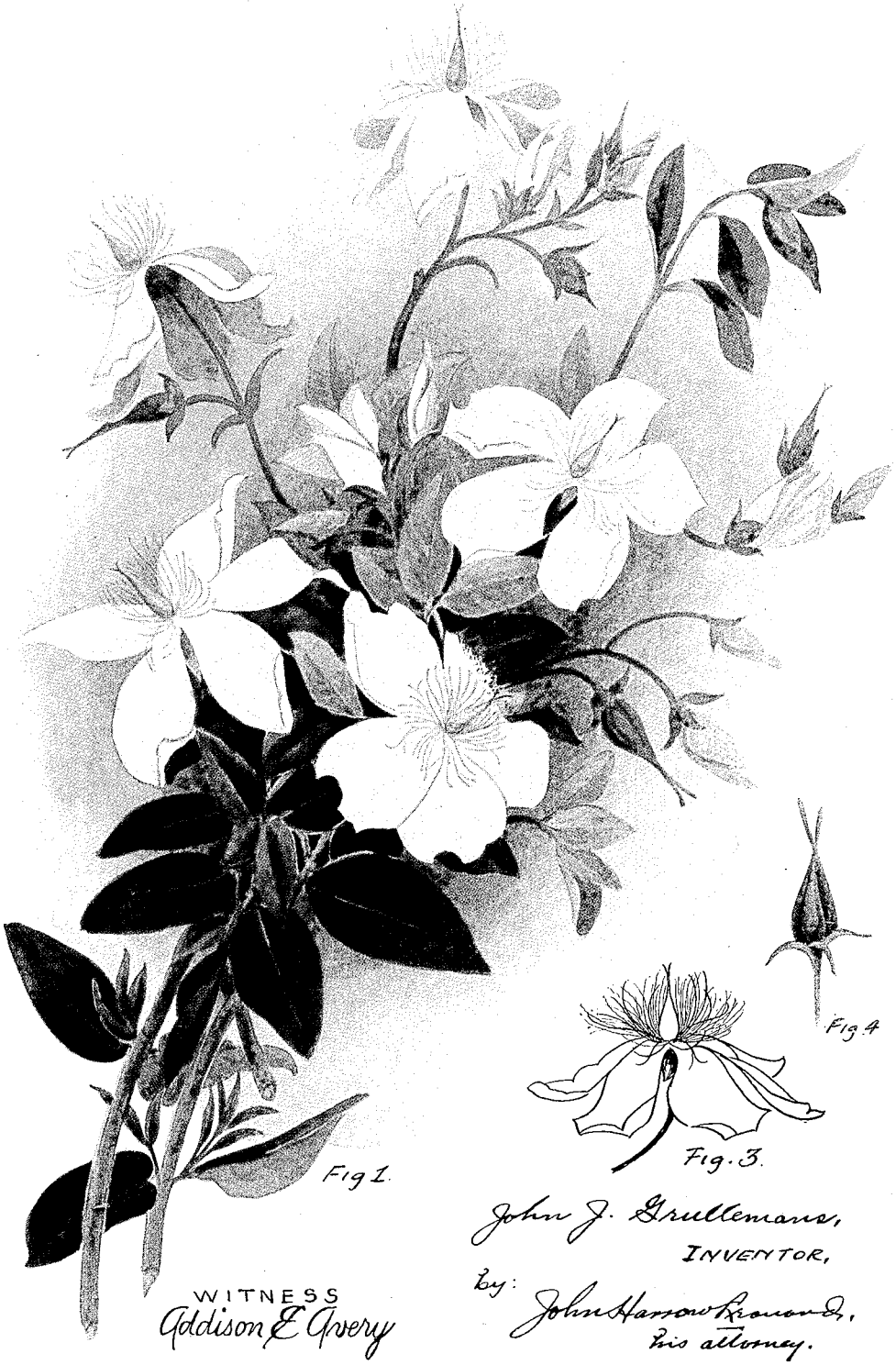
Fig. 1 is a color illustration disclosing the wood, leaves, buds and blossoms of the plant.
Figure 2:
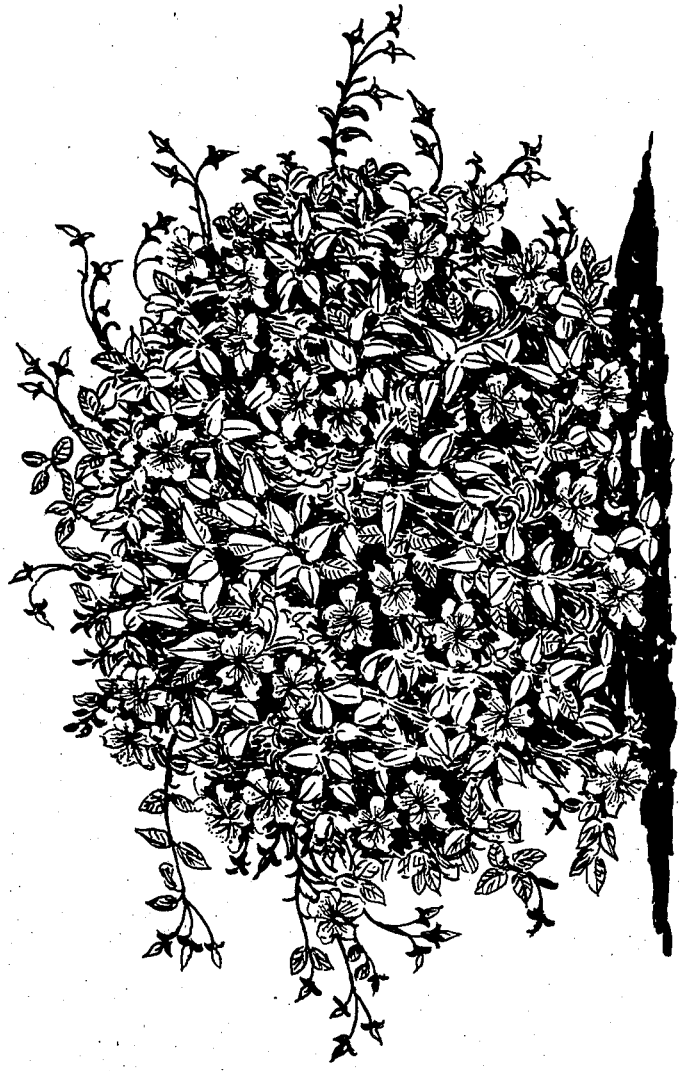
Fig. 2 is a sketch on a reduced scale illustrating the general shape of the exposed plant and recurvation of the branches.

The variety is one of the largest of the patulum hybrids, is entirely free from disease and can withstand excessive wetness and severe drouth. It thrives in a hot and dry location. Its winter resistance is exceptional for a Hypericum and, unprotected, it has withstood sustained temperatures from 20 to 25° F. without freezing back to the ground and the roots have withstood temperatures of 10° below zero without damage. The old wood freezes back to the snowline and produces new canes on the previous year's wood fifteen to eighteen inches long which flower as heavily as new wood produced from the base. In general it has withstood the winters of northern Ohio from 1935 to and including the winter of 1941–42 without freezing completely back to the ground.

Not only is the plant hardier than patulum varieties now in commerce but also the flowers are larger and the plant is differently formed, having partaken of the characteristics of both the parents, one of which is drooping and the other of which is upright, with the result that the stalks are recurvate, giving the plant a graceful mound-like and semi-weeping appearance.

The plant prefers sun and a southern exposure and is rather indifferent as to soil, though well drained soil is preferred, if any. Shade reduces the number of blooms and results in a tendency towards paling in the color.

The plant blooms continuously for a period of about two months, beginning the middle of June and ending the middle of August, and is covered with a myriad of blossoms.

The roots are of the usual woody structure but larger than the roots of other patulum hybrids. The plant is woody, compact and bush-like and grows to about two to three feet in height with a spread of two to three feet, both the size and mound-like shape being unusual.

Near the center of the bush, the stalks start generally upright and so extend almost to the full height of the stalk then bend outwardly in a graceful curve to their extremities which are drooping. As the outer limits of the plant are approached the stalks start from the ground at a progressively lesser angle to the horizontal until the outermost stalks start almost horizontally, but the terminal portions of the stalks all curve outwardly and downwardly, with the distinct drooping or pendulousness at the termini. The plant is exceedingly vigorous in growth.

The new wood is not much branched but wood two years old is very much branched. The new wood from the roots usually grows to a length of three to four feet, whereas the new growth on old wood is from six to twelve inches. The new wood from the roots is generally stiff and brittle but adequate to support the foliage and bloom well. Its color is between Hazel and Chipmunk, comparable to Maerz and Paul Plate No. 13–K–9. Many of the new branches are of an attractive color, comparable to Saraband, Maerz and Paul Plate No. 6–K–8.

The leaf arrangement varies greatly throughout the plant and is more or less indiscriminate, the leaves being very sparse toward the center of the plant and on the inner stalks but abundant at and near the terminals. The leaves are relatively large and of average thickness. Their persistency on the plant is excellent.

The new leaves are usually of a grass green comparable to Maerz and Paul Plate No. 21–L–5. The older leaves are green comparable to Maerz and Paul Plate No. 24–L–4 on the upper surface, and water green, comparable to Maerz and Paul Plate No. 19–C–2, on the under surface.

The buds are somewhat elongated and large for a hypericum and are pointed. They are supported in a leaning, or drooping and somewhat pendulous position. When the sepals first divide, the color of the exposed petals is a yellow, comparable to Maerz and Paul Plate No. 10–L–1, which deepens to a golden yellow, comparable to Maerz and Paul Plate No. 10–L–7, when the petals begin to unfurl.

When the flower is in full bloom the petals are Light Chrome YP, comparable to Maerz and Paul Plate No. 10–L–4. Toward the center of the flower the color deepens to a yellow comparable to Maerz and Paul Plate No. 17–K–2. The base of the buds is tipped with a color comparable to olive wood, Maerz and Paul Plate No. 15–E–10. The flowers are usually borne in clusters on peduncles about one and one-half inches long, the pedicels being about one-half inch long, thus providing a compound inflorescense, usually in clusters of three with frequent secondary and tertiary branches of three. The blossoms are about fifty percent larger than is usual for a hypericum and are borne in such a large number that they almost entirely cover the plant. Their permanence on the plant is good.

The shape of the flower is very distinct. Usually in Patulum hybrids the flower is in the form of a rather deep cut formed of upwardly concave petals. In the present hypericum, there is a reflexure or recurvation of the petals so that the flower is widely open with pronounced recurvation of the margins. In their normal fully bloomed condition the flowers are two to three inches in diameter. Due to the recurvation and open condition of the flower, the brilliant yellow stamens, of which there is an exceptionally large number, are very strikingly displayed and add to the apparent size and shape of the flower. The petals are of smooth waxy texture. The stamens, as stated, are unusually numerous, there being from about one hundred and fifteen to one hundred and seventy to a blossom. They are pale yellow but the shade is of such character that it is difficult to compare with the color charts. They are shown in the drawings slightly darker than their true color as otherwise they would not show in their proper relation to the blossom. By showing the stamens slightly darker than the true color the pictured blossoms give a true and correct impression of the actual blossoms and stamens.

Another unusual feature of the plant is the seed carpels which are generally of the usual shape except that they are somewhat larger and have an usual color when mature. The average shade is a Chianti Antique Ruby comparable to Maerz and Paul Plate No. 6–L–6, but this color varies somewhat in intensity and shading for different carpels, thus giving the plant an attractive appearance even after the petals have dropped.

The new variety is distinguished principally by the mound-like and semi-weeping appearance of the plant; the manner of growth and pendulousness of the extremities of the stalks; the exceptional hardiness for a hybrid Hypericum; the unusual floriferousness of the plant as a whole; the large size and rich golden yellow color of the flowers; the reflexure or recurvation of the petals so as to make the stamens more conspicuous; the large number and conspicuousness of the stamens themselves; the seed carpels which are of an attractive variegated color at maturity; the lasting quality of the flowers when cut and particularly their beauty as cut flowers due to the long arching stems on which they are supported.

Having now fully shown and described my new hypericum, and the mode of its production, what I claim and desire to secure by Letters Patent of the United States is:

A variety of Hypericum herein shown and described, characterized by its exceptional hardiness, the recurvation of the wood creating a mound-like and semi-weeping appearance of the plant as a whole, the reflexure and recurvation of the petals of each flower, large number of conspicuous stamens, the rich color of the individual flowers, the exceptional floriferousness of the plant and the manner in which the flowers are borne, the unusual color of the seed carpels and the large number of flowers in bloom concurrently, and the lasting quality as cut flowers.

JOHN J. GRULLEMANS.

CERTIFICATE OF CORRECTION.

March 2, 1943.

Plant Patent No. 568.

JOHN J. GRULLEMANS.

It is hereby certified that error appears in the printed specification of the above numbered patent requiring correction as follows: Page 2, first column, line 17, for "cut" read --cup--; and that the said Letters Patent should be read with this correction therein that the same may conform to the record of the case in the Patent Office.

Signed and sealed this 13th day of April, A. D. 1943.

Henry Van Arsdale,
Acting Commissioner of Patents.

(Seal)